United States Patent [19]

Wang et al.

[11] Patent Number: 4,636,535
[45] Date of Patent: Jan. 13, 1987

[54] CURABLE EPOXY RESIN COMPOSITIONS

[75] Inventors: David W. Wang, Vestal, N.Y.; Jeanne L. Courter, Stamford; Dalip K. Kohli, Norwalk, both of Conn.

[73] Assignee: American Cyanamid Company, Stamford, Conn.

[21] Appl. No.: 691,993

[22] Filed: Jan. 16, 1985

Related U.S. Application Data

[63] Continuation-in-part of Ser. No. 518,872, Aug. 1, 1983, abandoned.

[51] Int. Cl.$^4$ .......................... C08K 3/34; C08K 3/04; C08K 3/02; C08L 61/00
[52] U.S. Cl. .................................... 523/204; 523/207; 523/448; 523/455; 523/457; 523/468; 525/417; 525/423; 525/438; 525/504; 525/523
[58] Field of Search ............... 523/204, 207, 468, 448, 523/457, 455; 528/124, 363, 365; 525/504, 417, 423, 438, 523

[56] References Cited

U.S. PATENT DOCUMENTS

| | | | |
|---|---|---|---|
| 3,932,360 | 1/1976 | Cerankowski et al. | 260/77.5 |
| 3,984,370 | 10/1976 | Shinohara et al. | |
| 4,191,835 | 3/1980 | Habermeier et al. | 528/64 |
| 4,283,549 | 8/1981 | Holm | 560/50 |
| 4,427,802 | 1/1984 | Moulton et al. | 523/222 |
| 4,532,275 | 7/1985 | Aito et al. | 525/423 |

FOREIGN PATENT DOCUMENTS

| | | |
|---|---|---|
| 1017612 | 1/1966 | Fed. Rep. of Germany . |
| 1024288 | 3/1966 | Fed. Rep. of Germany . |
| 1182377 | 2/1970 | Fed. Rep. of Germany . |
| 52-74655 | 6/1977 | Japan . |
| 1141206 | 1/1969 | United Kingdom . |
| 2040956 | 9/1980 | United Kingdom ................ 523/448 |

OTHER PUBLICATIONS

Gillham et al., Organic Coatings and Applied Polymer Science Proceedings, vol. 46, pp. 592–598, Mar.–Apr. 1982.
Gillham et al., Organic Coatings and Applied Polymer Science Proceedings, vol. 46, pp. 566–570, Mar. 1983.
Gillham et al., Organic Coatings and Applied Polymer Science Proceedings, vol. 48, pp. 571–575, Mar. 1983.
Misra et al., Network Morphology and the Mechanical Behavior ACS Symposium Series #114, pp. 157–182, 1979.

*Primary Examiner*—Lewis T. Jacobs
*Attorney, Agent, or Firm*—William H. Calnan

[57] ABSTRACT

Curable compositions are provided comprising epoxide prepolymers and polyaminobenzoates, alone, or combined with reinforcements, e.g., graphite fibers, and, optionally modified with second resins. The cured fiber resin matrix compositions exhibit high toughness combined with excellent hot/wet strength.

36 Claims, 3 Drawing Figures

CURABLE EPOXY RESIN COMPOSITIONS

This application is a continuation-in-part of Ser. No. 518,872, filed Aug. 1, 1983, now abandoned.

FIELD OF THE INVENTION

This invention relates to improved reinforced epoxy resin compositions. In addition, it relates to curable epoxy resin compositions comprising non-siliceous reinforcing filaments and epoxy prepolymers combined with aromatic polyamine curing agents.

CROSS-REFERENCE

The following applications, filed concurrently Aug. 1, 1983, are related:

| Serial No. | Applicant(s) |
| --- | --- |
| 518,871 | R. P. Krieger, Jr., K. Hirschbuehler, R. P. Politi |
| 518,872 | D. W. Wang, J. L. Courter, D. K. Kohli |
| 518,863 | D. K. Kohli |
| 518,873 | K. Hirschbuehler |
| 518,874 | K. Hirschbuehler, D. K. Kohli D. R. Draney, D. K. Kohli |
| 518,856 | D. W. Wang, D. R. Draney |
| 518,875 | K. Hirschbuehler |

BACKGROUND OF THE INVENTION

Fiber resin martices comprised of curable epoxy resin compositions and fiber reinforcement have found extensive use in applications where high strength, corrosion resistance and light weight are desired. Considerable effort has been expended in improving the properties and performance of such fiber resin matrix compositions, including the development of many different curing systems.

Amine and polyamine curing agents, such as m-phenylenediamine, 4,4'-diaminodiphenyl methane and diamino diphenyl sulfone (DDS), have become widely accepted. However, their characteristic toxicity, low solubility, high exotherm and variable curing rate has made further improvement in curing systems desirable.

In U.K. Pat. No. 1,182,377, a number of aromatic polyamines falling within the broad formula:

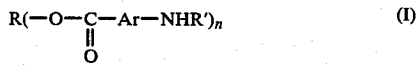

wherein R is the radical formed after elimination of the hydroxyl groups of a polyhydric aliphatic, cycloaliphatic or araliphatic alcohol, Ar is an optionally substituted phenylene or naphthylene radical, R' is hydrogen or alkyl and n is an integer of 2 to 10, have been investigated as curing agents. They are reported to be less toxic and to provide less cracking when used as curing agents in epoxy compositions for glass-reinforced fiber resin matrices. It is also known from Moulton et al, U.S. Pat. No. 4,427,802, that aromatic polyamines can be modified prior to use by reaction with carbonyl compounds to avoid the drawbacks associated with all polyamines. Finally, Asahi, Japan 52-74665 (1977), teaches that if polyamine curing agents are used with tetrafunctional epoxy resins, carbon fiber-reinforced composites having excellent interlaminar strength and heat resistance will be provided.

From such disclosures it would be expected that all of the polyamine compounds described in U.K. Pat. No. 1,182,377 (formula (I), above) would give beneficial results in carbon fiber-reinforced composites. In fact, however, such expected benefits have not been found, and, when some of the compounds exemplified in U.K. Pat. No. 1,182,377 are substituted for the polyamine curing agents in the matrix resins of the Moulten et al or the Asahi patent compositions, gross deficiencies in physical properties occur, as will be demonstrated hereinafter.

It has now been discovered that the role of the bridging group designated R in compounds of the formula (I) above, is surprisingly more important in determining the ultimate physical properties and performance-in-use of the final fiber resin matrix composite than has been realized before by those skilled in this art. Applicants herein have discovered that the structural nature of the R radical has a profound effect on such properties, e.g., as glass transition temperature, flexibility and toughness in cured carbon fiber-reinforced epoxy resin composites. Moreover, it appears in some cases that these disparate effects are unique to non-siliceous fiber-reinforced resin matrixes and cannot be predicted from testing cured neat resin compositions or glass-reinforced resin composites. As will be demonstrated in comparative examples herein, the degree of branching, the chain length, and the steric bulk of the bridging R radical are all factors in the performance of the final fiber resin matrix composite. For example, a high degree of branching, such as where R is dialkylpropylene, tends to lower the glass transition temperature, flexibility and toughness of the fiber resin matrix; the length of alkyl or alkoxy chains in the R radical also affects properties, longer chains tending to lower the cross-link density of the cured resin, resulting in a lowered glass transition temperature; and the presence of bulky groups such as phenylene radicals also appears to lower rotational freedom or contribute steric bulk to the compound, and this leads to an undesirable decrease in the glass transition temperature.

It is a key feature of the present invention to judiciously select aromatic diamine curing agents for curable epoxy resin compositions to provide superior physical properties and performance in use after curing. Such selection will necessarily omit the compounds of the working examples of the U.K. Pat. No. 1,182,377, many of which are functionally characterized by bridging R radicals which adversely affect the properties of non-siliceous fiber-reinforced epoxy resin composites. The reinforced compositions prepared according to this invention show improved interlaminar toughness and residual compression strength, while maintaining compression strength under hot/wet conditions.

The present invention is directed to heat-curable epoxy resin compositions having non-siliceous fiber reinforcement and including a selected diamine curing agent of the general formula:

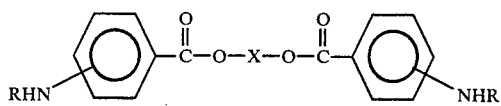

(II)

wherein R is hydrogen or methyl and X is a divalent non-aromatic organic hydrocarbon, non-aromatic hetero-interrupted hydrocarbon, or non-aromatic halo- or alkyl-substituted hydrocarbon radical. In the preferred curable resin compositions of this invention, divalent X radicals will be selected to minimize branching, chain length and steric bulk, and thereby maintain excellent performance under hot and hot/wet conditions, e.g., high glass transition temperature (e.g., of 100° C. or above) and compression strength. The superior performance of such compositions is shown in many of the working examples that follow.

SUMMARY OF THE INVENTION

It is an object of the present invention to provide improved epoxy resin compositions.

It is a further object of the present invention to provide a fiber resin matrix composition that affords satisfactory compression strength over known matrix formulations, especially under hot/wet conditions, and improved compression strength after impact.

It is a further object of the present invention to provide fiber resin matrix compositions that have superior toughness in comparison with materials known in the prior art and which maintain high glass transition temperatures and compression strength under hot and hot/wet conditions.

These and other objects are accomplished herein by a fiber resin matrix composition comprising:
(a) non-siliceous reinforcing filaments, and
(b) a heat-curable epoxy resin composition comprising:
  (i) an epoxy prepolymer or combination of prepolymers having more than one epoxide group per molecule, and
  (ii) an amount effective to promote cure of an amine-functional curing agent or combination of curing agents selected from those of the formula:

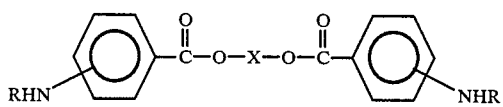

(II)

wherein R is hydrogen or methyl, and X is a divalent non-aromatic organic hydrocarbon, non-aromatic hetero-interrupted hydrocarbon, or halo- or alkyl-substituted hydrocarbon radical. Preferably the structure of the X divalent radical is characterized in that it confers on cured fiber resin matrices improved interlaminar toughness and residual compression strength after impact, while maintaining compression strength under hot/wet conditions. In preferred fiber resin matrix compositions the diamine curing agent is selected to maintain a hot/wet glass transition temperature of 100° C. or greater.

When used herein and in the appended claims, the expression "improved interlaminar toughness and residual compression strength after impact" refers as a basis for comparison to the exemplified compounds of U.K. Pat. No. 1,182,377, particularly to the curing agent of Example 5 therein.

In other features of this invention, the heat-curable epoxy resin composition (b) will also include other amines, e.g., diamino diphenyl sulfone, bis(3-aminophenoxy diphenyl sulfone, bis(4-aminophenoxy diphenyl sulfone, diaminobenzophenone, phenylene diamine, methylene dianiline, and the like, as curing co-agents; catalysts, e.g., dicyandiamide (DICY), the reaction product of toluene diisocyanate and dimethyl amine, the reaction product of phenyl isocyanate and N,N'-diethyl-1,3-propane dimaine, boron trifluoride-/organic amine complexes, etc.; thermoplastic modifiers, rubber modifiers, and bismaleimide modifiers described hereinafter; and fillers, e.g., fumed silica and others. Selection of such additional components provides a broad spectrum of high performance fiber resin matrix composites having unique physical properties and advantages unobtainable with prior art compositions.

Most preferably, the present invention contemplates non-siliceous fiber reinforced heat-curable epoxy resin compositions comprising:
(i) an epoxy prepolymer or combination of prepolymers having more than one epoxide group per molecule, and
(ii) an amount effective to promote cure of an amine-functional curing agent or combination of curing agents selected from those of the formula:

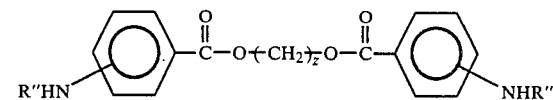

wherein R" is hydrogen or methyl, and z is an integer of from 2 to 10, preferably 3. Special mention is made of the compounds in which R" is hydrogen or methyl, z is 3 and the amino substituents are fixed in the 4 and 4' positions.

It is among the features of this aspect of the invention to provide embodiments which are useful as prepregs, for example, to make laminates and other structural shapes in accordance with procedures known in this art.

In another preferred feature of the invention, the fiber resin matrix compositions will comprise:
(a) non-siliceous reinforcing filaments, and
(b) a heat-curable epoxy resin composition formed of the following materials:
  (i) N,N,N',N'-tetraglycidyl-4,4'-diaminodiphenyl methane, e.g., 50 to 100, preferably 75 to 85, parts by weight,
  (ii) tetraglycidoxy tetraphenylethane, e.g., 0 to 50, preferably 15 to 25, parts by weight;
  (iii) trimethylene bis(p-aminobenzoate), e.g., 28 to 60, preferably 35 to 45, parts by weight;
  (iv) fumed silica, e.g., 0 to 12, preferably 5 to 7, parts by weight, and
  (v) the reaction product of toluene diisocyanate and dimethylamine, e.g., 0.1 to 2.5, preferably 0.5 to 1.5, parts by weight.

The fiber resin matrix compositions are uniquely suitable for use with an interleaf material to prepare a mechanically superior cured structure.

In another preferred feature, the present invention provides epoxy resin compositions including the above-mentioned diamine curing agents and also including a second resin in an amount sufficient to impart improvements in mechanical properties, especially toughness, while preserving substantial resistance to failure under hot/wet conditions. Such resins can be present homogeneously or heterogeneously and also in the form known as interpenetrating polymer networks. Particularly useful in this apsect are resins which include repeating units of the formula:

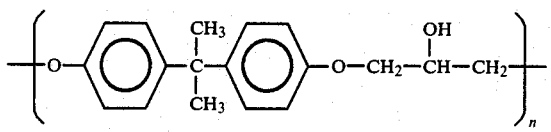

and those with repeating units of the formula:

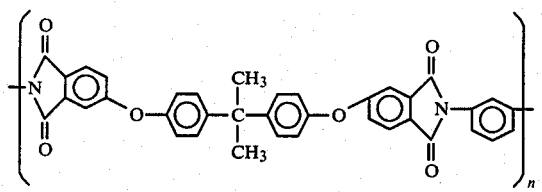

wherein n is a number sufficient to provide a molecular weight of 20,000 to 60,000. Amounts of 5 to 30, preferably 10 to 20, parts by weight per 100 parts by weight of epoxy prepolymer can be used.

DESCRIPTION OF THE PREFERRED EMBODIMENTS

Figure 1:
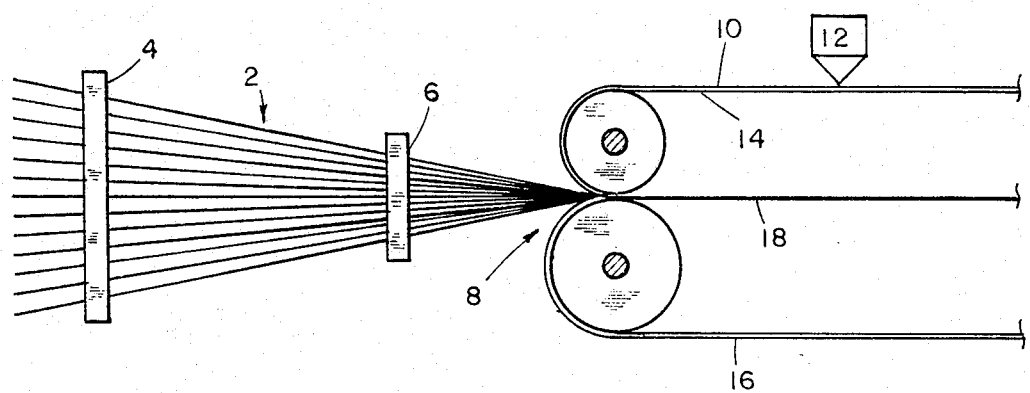
FIG. 1 is a schematic of one method for preparing a fiber resin matrix prepreg tape of the present invention.

In general, the resin compositions of this invention are prepared by mixing the polyepoxide compounds with the polyamines of the above-mentioned formula (II) in conventional quantitive ratios, e.g., 1 epoxide equivalent to 0.3 to 3.0 NH— equivalents, preferably 0.5 to 1.5 NH— equivalents, and especially preferably 0.7 to 1.0 NH— equivalents, optionally with heating, e.g., at a temperature in the range of 30° C. to 300° C., preferably at a temperature in the range of 80° C. to 180° C., until a melt is obtained. The melt can then be poured into a mold and reacted, for example, for 2 hours at 135° C. and then for 3 hours at 180° C., to form moldings showing outstanding mechanical and electrical properties. The NH— equivalents is the quantity of aromatic polyamine in grams in which 1 gram-atom of hydrogen combined with amine nitrogen is present.

Fillers, pigments, dyes, reinforcements (such as carbon fibers or woven cloths), plasticizers, and mixtures thereof, may be added to the epoxy resin-polyamine composition before the reaction in order to modify ultimate properties, in known ways. Applications can also be made by trowelling, brush coating, immersion or dip-coating, spraying and other convenient methods. Catalysts, such as boron trifluoride-organic amine adducts, and the reaction product of toluene-2,4-diisocyanate and dimethylamine can also be introduced, in quantities of from, e.g., 0.1% to 5% by weight based on the resin-polyamine, to accelerate curing.

The fiber resin matrix compositions according to the present invention can be prepared by embedding filaments, e.g., non-siliceous filaments such as carbon fibers, graphite fibers, etc., in a curable resin composition to form a fiber resin matrix which can be manipulated and cured to a solid composite. Particular selection, in accordance with this invention, of the filament material, epoxy prepolymer and diamine curing agent, as well as including optional ingredients such as fillers, dyes, catalysts, processing aids, etc., can give a range of curable compositions heretofore unknown in the art and exhibiting improved physical properties over known materials.

The non-siliceous filament component may be of any nonglass, non-silicon dioxide-containing material which improves the strength or other physical properties of the curable epoxy resin component (described infra.). Such filaments, include, but are not limited to, filaments comprised of carbon (e.g., graphite), silicon carbide, boron, aramid, polyester, polyamide, rayon, polybenzimidazole, polybenzothiazole, metal-coated such filaments, for example nickel-coated and/or silver-coated graphite fibers and filaments, or combinations of such filaments. Fibers (woven or non-woven), tows or mats of such filaments, or tapes (unwoven, flat bundles of the unidirectional filaments) may be employed as desired. In applications demanding high stiffness to weight ratios or shear strength, carbon fibers, especially graphite filaments, polyaramid filaments or nickel-plated graphite filaments, as disclosed in published European Patent Application No. 8310195.2, are most peferred.

The epoxy resins suitable for the present invention are compounds having more than one epoxide group per molecule available for reaction with the primary and secondary polyamines of the present invention (described infra.). Such epoxy prepolymers include but are not limited to polyglycidyl ethers of polyvalent phenols, for example pyrocatechol; resorcinol; hydroquinone; 4,4'-dihydroxydiphenyl methane; 4,4'-dihydroxy-3,3'-dimethyldiphenyl methane; 4,4'-dihydroxydiphenyl dimethyl methane; 4,4'-dihydroxydiphenyl methyl methane; 4,4'-dihydroxydiphenyl cyclohexane; 4,4'-dihydroxy-3,3'-dimethyldiphenyl propane; 4,4'-dihydroxydiphenyl sulphone; or tris-(4-hydroxyphenyl) methane; polyglycidyl ethers of the chlorination and bromination products of the above-mentioned diphenols; polyglycidyl ethers of novolacs (i.e., reaction products of monohydric or polyhydric phenols with aldehydes, formaldehyde in particular, in the presence of acid catalysts); polyglycidyl ethers of diphenols obtained by esterifying 2 mols of the sodium salt of an aromatic hydroxycarboxylic acid with 1 mol of a dihalogenalkane or dihalogen dialkyl ether (U.K. Pat. No. 1,017,612); and polyglycidyl ethers of polyphenols obtained by condensing phenols and long-chain halogen paraffins containing at least 2 halogen atoms (U.K. Pat. No. 1,024,288).

Other suitable compounds include polyepoxy compounds based on aromatic amines and epichlorohydrin, for example N,N'-diglycidyl-aniline; N,N'-dimethyl-N,N'-diglycidyl-4,4'-diaminodiphenyl methane; and N-diglycidyl-4-aminophenyl glycidyl ether. Special mention is made of N,N,N',N'-tetraglycidyl-1,3-propylene bis-4-aminobenzoate.

Glycidyl esters and/or epoxycyclohexyl esters of aromatic, aliphatic and cycloaliphatic polycarboxylic acids, for example phthalic acid diglycidyl ester and adipic ester diglycidyl and glycidyl esters of reaction products of 1 mol of an aromatic or cycloaliphatic dicarboxylic acid anhydride and ½ mol or a diol or 1/n mol of a polyol with n hydroxyl groups, or hexahydrophthalic acid diglycidyl esters, optionally substituted by methyl groups, are also suitable.

Glycidyl ethers of polyhydric alcohols, for example of 1,4-butanediol; 1,4-butanediol; glycerol; 1,1,1-trimethylol propane; pentaerythritol and polyethylene glycols may also be used. Triglycidyl isocyanurate; and polyglycidyl thioethers of polyvalent thiols, for example of bis-mercaptomethylbenzene; and diglycidyltrimethylene sulphone, are also suitable.

Preferably the epoxy prepolymer component will be selected from compounds having the idealized formula:

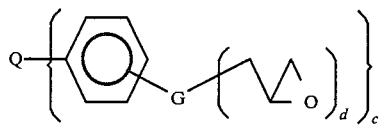

and halogen and alkyl substituted derivatives of such compounds, wherein c is 2, 3 or 4 and equal to the valence of Q; Q is a divalent, trivalent or tetravalent radical; G is —O—, —NR'— or

R' is hydrogen or alkyl; and d is 1 or 2 depending on the valence of G.

The most preferred epoxy compounds will include the following:

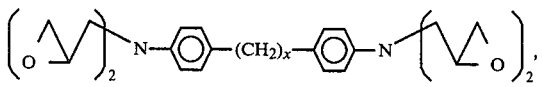

wherein x is an integer from 1 to 4, available commercially (where x=1) as Araldite® MY-720 (Ciba-Geigy);

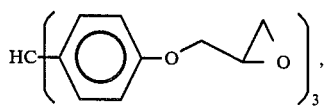

available commercially as XD7342 (Dow Chemical);

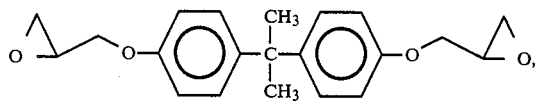

available commercially as DER® 331 (Dow Chemical) or EPON® 828 (Shell);

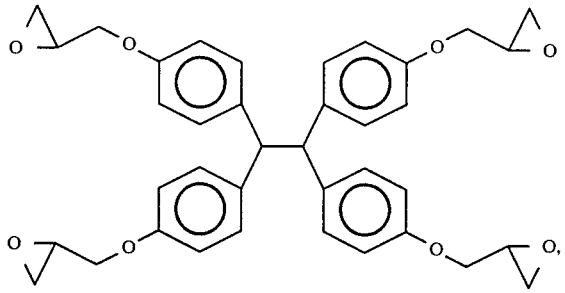

available commercially as EPON® 1031 (Shell);

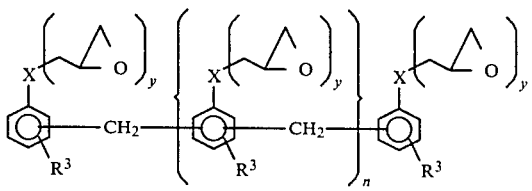

wherein y is 1 or 2, X is —O— or

$R^3$ is H or $CH_3$ and n is 2 to 8.

Compounds in which X is —O— are available as a mixture under the tradename DEN® 438 from Dow Chemical Company.

Also preferred are triglycidyl ethers of meta- and para-hydroxyaniline, e.g., represented by the formula:

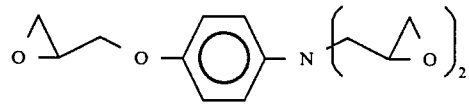

These are available under the tradename ARALDITE® 0500, 0510 from Ciba-Geigy.

The polyamine curing agents are of the formula:

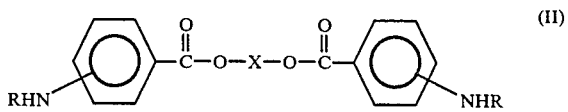

(II)

wherein R is hydrogen or methyl and X is a divalent non-aromatic organic hydrocarbon, non-aromatic hetero-interrupted hydrocarbon, or non-aromatic halo- or alkyl-substituted hydrocarbon radical, and exhibit higher toughness than achieved in systems of the prior art, while maintaining the hot/wet performance of the other materials. Suitable such radicals include divalent polymethylene chains of 2–10 carbon atoms, branched alkylene chains of no more than 12 carbon atoms and wherein there is no more than one alkyl branching group per main-chain carbon atom, halogen-substituted hydrocarbon radicals, cyano radicals, linear dialkyl ether radicals, and the like. They may be prepared from corresponding starting materials, e.g., nitro compounds, by reduction, for example, according to methods described in U.K. Pat. No. 1,128,377. In addition, commonly assigned U.S. application Ser. No. 518,863 shows an elegant method for N-methylation, using succinimide and formaldehyde with the primary amine, followed by reductive cleavage.

As mentioned above, the bridging divalent radical, X, desirably has a short chain length, e.g., 12 or less, preferably less than 6, carbons; has a low degree of branching, e.g., 1-3 alkyl branches of 1 or 2 carbons on an alkylene radical of 10 carbons or less; and has few bulky structures or substituent groups, e.g., phenylene, which hinder rotational freedom of the diamine compound or contribute steric bulk. Selecting the X divalent radical accordingly has been discovered to contribute to high glass transition temperature, Tg, in the reinforced epoxy compositions and to improve their compression strength under hot and hot/wet conditions.

Suitable curing agents include compounds according to the above formula (II) in which R is hydrogen or methyl and X is a divalent radical selected from the group consisting of, e.g., polymethylene of from 1 to 10 carbon atoms, —CH$_2$CH$_2$—O—CH$_2$CH$_2$—, —(CH$_2$CH$_2$O)$_2$—CH$_2$CH$_2$—,

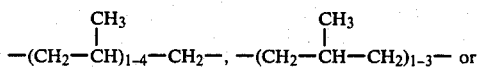

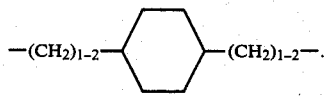

Preferred curing agents include:

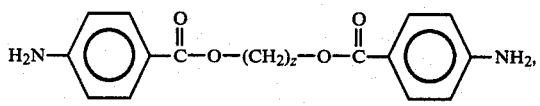

wherein z is an integer of from 2 to 10, preferably 2 to 6;

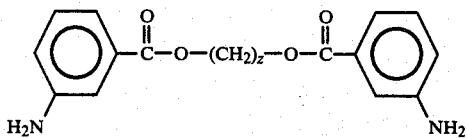

wherein z is an integer from 2 to 10, preferably 2 to 6,

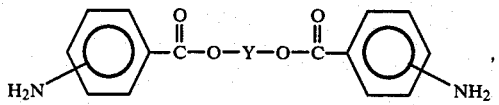

wherein Y is —CH$_2$CH$_2$OCH$_2$CH$_2$OCH$_2$CH$_2$—, —CH$_2$CH$_2$OCH$_2$CH$_2$—, —CH$_2$CH$_2$CH(CH$_3$)CH$_2$CH$_2$—, —CH$_2$CH(CH$_3$)CH$_2$CH$_2$CH$_2$—,

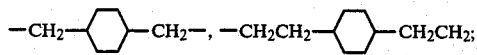

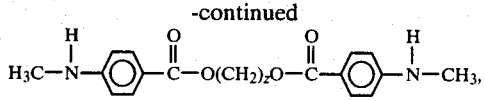

wherein z is an integer of from 2 to 10, preferably 2 to 6;

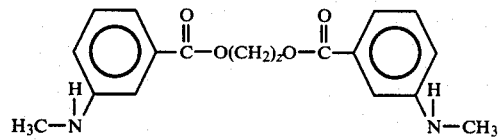

wherein z is an integer of from 2 to 10, preferably 2 to 6;

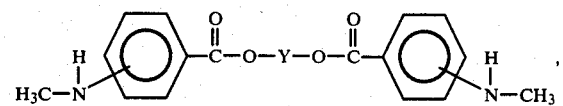

wherein Y is —CH$_2$CH$_2$OCH$_2$CH$_2$OCH$_2$CH$_2$—, —CH$_2$CH$_2$OCH$_2$CH$_2$—, —CH$_2$CH$_2$CH(CH$_3$)CH$_2$CH$_2$—, —CH$_2$CH(CH$_3$)CH$_2$CH$_2$CH$_2$—,

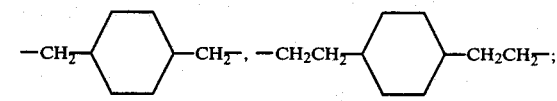

In the most preferred compositions, the diamine curing agent will include one or more compounds of the formula:

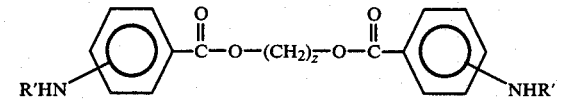

wherein R' is hydrogen or methyl, and z is an integer of from 2 to 10, preferably 2 to 6, and most preferably 3. Also contemplated are the use of such compounds in combination with other conventional polyamines such as methylene dianiline, bis-3- or 4-aminophenoxy diphenyl sulfone, diaminobenzophenone, phenylene diamine, and the like.

The fiber resin matrix composition of the invention may be formed by the method illustrated in the drawings. As seen in FIG. 1, the basic fiber matrix material is produced by delivering non-siliceous fiber 2 through conventional eyeboards 4 and 6 to a pressure roller assembly 8. The resin composition is coated in a layer 10 from a conventional film coating applicator 12 onto a substrate such as release paper 14 and passed through the pressure roller assembly 8. Release paper 16 is also delivered to the pressure roller assembly 8.

The pressure rollers 8 are set at a temperature and pressure for imbedding the fibers 2 in the resin layer 10 to form a fiber matrix composition 18. Practice has taught that a temperature in the range of 190° F. and pressures of one thousand pounds over fifteen inch centers are suitable for producing fiber resin prepreg tape 18.

The fibers 2, the substrate 14 with resin layer 10 and the release paper 16 are delivered to the pressure rollers 8 and passed therethrough at the rate of 5-20 feet/minute.

The feed of fiber 2 and resin layer 10 to the pressure rollers 8 is selected to produce a fiber matrix of about twenty to sixty weight percent resin and about eighty to forty weight percent fiber. For example, one hundred twenty spools of 6K carbon fibers are delivered within a twelve inch width to the pressure rollers 8 with a layer of resin 0.009 to 0.0013 pounds per square foot. The resulting fiber resin matrix 18 results in a generally parallel array of fibers, shown by FIG. 2.

Fillers, pigments, dyes, curing catalysts and other such conventional additives and processing aids may be added to the fiber matrix compositions of the invention before curing to influence the properties of the final resin composite. In addition, polymeric additives such as the butadiene-styrene-acrylonitrile core-shell polymers and the like can be included for their known effects on polymer properties.

The following examples will illustrate the practice of the present invention and are provided by way of demonstration and not by way of limitation.

EXAMPLES 1-10

A series of compositions was prepared in order to compare diamine curing agents of this invention with those of the prior art. Several diamine curing agents were investigated, including: 1,3-trimethylene bis(p-aminobenzoate) (FD-1),

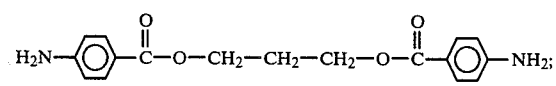

Diamino diphenyl sulfone (DDS),

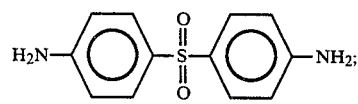

and other polyamines having various bridging structures (i.e., the X radicals, in formula (II)) linking the two aminobenzoate groups, 2,2-dimethylpropylene-bis(m-aminobenzoate) (DP-mAB),

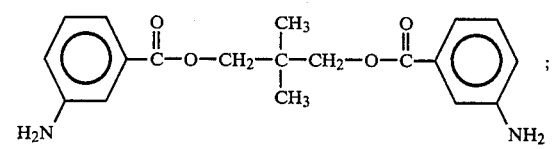

triethoxyethylene-bis(p-aminobenzoate) (TE-pAB),

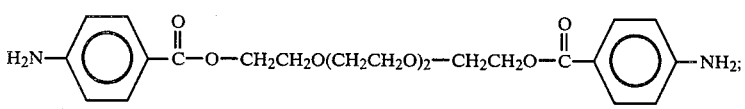

p-dimethylenephenylene-bis(m-aminobenzoate) (pDMP-mAB),

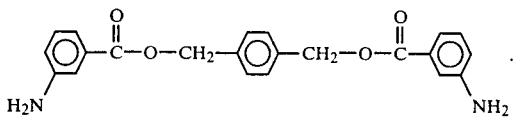

The chemical formula of the epoxy resin used, CIBA-GEIGY MY-720, is as follows:

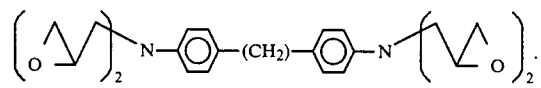

The matrix resins in the graphite fiber-reinforced and the glass fiber-reinforced composites were formulated as follows:

| Sample | Fabric | Epoxy | Amine |
|---|---|---|---|
| 1 | Graphite | MY-720 | FD-1 |
| 2* | Graphite | MY-720 | DDS |
| 3* | Graphite | MY-720 | DP-mAB |
| 4* | Graphite | MY-720 | TE-pAB |
| 5* | Graphite | MY-720 | pDMP-mAB |
| 1A* | Glass | MY-720 | FD-1 |
| 2A* | Glass | MY-720 | DDS |
| 3A* | Glass | MY-720 | DP-mAB |
| 4A* | Glass | MY-720 | TE-pAB |

*not according to this invention

The graphite laminates were reinforced with graphite fabric grade 3K1358H made from Union Carbide's Thornel® 300 carbon fiber, having an areal weight (weight per area) of 364 g/sq. m. The glass laminates were reinforced with fabric grade 7781-UM731 with an areal weight of 311 g/sq. m. The fabrics were coated with the epoxy/amine mixture according to the above formulations, using an epoxy/amine ratio of 1:0.75 and using the following procedure:

A piece of fabric 25" in the warp direction by 42" in the fill direction was cut. The fabric was then taped to the base of a fume hood that had been covered with Teflon coated glass fiber (to provide a clean and releasing surface). The amount of resin to be used was calculated by measuring the area of the fabric and using the areal weight to calculate a fabric weight. The weight of resin needed to give a 40% resin and 60% (by weight) fabric was used. This weight ratio provides a 50 volume percent resin composite. The weights of the epoxy and amine needed to give the total weight of resin were calculated. The epoxy, MY-720, was then dissolved in approximately 200 ml. of methylene chloride and the amine was dissolved in approximately 150 ml. of acetone. The two solutions were then mixed. Some of the solution was poured onto the fabric and spread with a roller until the whole piece of fabric was coated. The material was then allowed to dry for approximately one hour, and then the remaining solution was poured onto the fabric and rolled out evenly. The material was then left to air dry in the hood overnight. The next day the impregnated fabric, called a "prepreg", was removed from the hood and placed in a well ventilated oven at 60° C. for 45 minutes to complete drying.

The graphite fabric prepreg was then formed into 8-ply symmetric laminates [(0,90)4]$_S$. The glass fabric prepreg was formed into 16-ply laminates. The laminates were cured by the following cure schedule: vacuum was applied at room temperature (RT) for 10 minutes, then the laminate was heated to 150° F. over a 20-minute period, and held at 150° F. for 15 minutes. Pressure of 100 psi was applied and the vacuum source was removed. It was then heated to 350° F. over a 30-minute period and held at 350° F. for 90 minutes. It was cooled to room temperature (RT) over a 40-minute period.

The laminates were tested as follows:

(I) Differential Scanning Calorimeter

The cure of the five epoxy compositions was compared using differential scanning calorimetry. The extent of reaction that took place during a cure at 180° C. for 90 min. was measured. In addition, the glass transition temperature (Tg) of the resin after cure was measured, heating at 10° C./minute. The results were as follows:

described in "A New Dynamic Mechanical Analysis System for Characterization of Physical Properties" by R. L. Blaine, P. S. Gill, R. L. Hassel, and L. Woo, Journal of Applied Polymer Science, Vol. 34, 1978. Samples were tested dry and after seven days immersed in deionized water at 82° C.

(III) Short Beam Shear Strength

This test was carried out at room temperature and 190° C. for dry samples. The test follows ASTM D2344 using ⅜"×1" specimens.

(IV) Compression Strength

Samples 4"×½" were tabbed leaving an ⅛" gauge section. The ends were machined for parallelism and the sample was tested to failure in compression using a test jig that provided lateral support at the tabs. This test was carried out at 190° C. for dry samples. Samples immersed in water for 13 days at 71° C. were tested in compression at 160° C.

(V) Interlaminar Strain Energy Release Rate (ISERR)

ISERR (abbreviated $G_{Ic}$ in the table) was measured using a width tapered double cantilever beam specimen. This test is described by W. D. Bascom, et al., *Composites*, 11:9 (1980). The sample's length was 6" and maximum width was 1"-¾".

TABLE 1
SUMMARY OF PROPERTIES

| SAMPLE | SUBSTRATE | MATERIAL | DMA (Tg) °C., Dry Tg | DMA (Tg) °C., Wet$^a$ Tg | SHORT BEAM SHEAR STRENGTH (KSI) | | COMPRESSION STRENGTH (KSI) | | $G_{Ic}$ (IN LB/IN$^2$) |
|---|---|---|---|---|---|---|---|---|---|
| | | | | | 23° C. DRY | 190° C. DRY | 190° C. DRY | 160° C. WET$^b$ | |
| 6 | graphite | MY-720/FD-1 | 245 | 202 | 9.53 ± .14 | 4.22 ± .10 | 54 ± 5 | 43 ± 3 | 1.29 |
| 7* | graphite | MY-720/DDS | 244 | 204 | 8.84 ± 1.34 | 4.68 ± .07 | 56 ± 5 | 45 ± 3 | 0.97 |
| 8* | graphite | MY-720/DP-mAB | 204 | 182 | 9.73 ± .55 | 1.72 ± .02 | 30 ± 2 | 30 ± 2 | 0.98 |
| 9* | graphite | MY-720/TE-pAB | 151 | — | 10.4 ± .2 | 0.52 ± .02 | 9 ± 1 | 7 ± 1 | 1.84 |
| 10* | graphite | MY-720/pDMP-mAB | 187 | — | 9.36 ± .49 | 0.89 ± .03 | 14 ± 1 | 15 ± 1 | 0.86 |
| 6A* | glass | MY-720/FD-1 | 247 | — | 10.6 ± .6 | 4.08 ± .15 | 57 ± 12 | 37 ± 3 | 1.96 |
| 7A* | glass | MY-720/DDS | 243 | — | 10.0 ± .1 | 5.33 ± .12 | 63 ± 6 | 40 ± 3 | 1.04 |
| 8A* | glass | MY-720/DP-mAB | 214 | — | 11.5 ± .1 | 1.96 ± .02 | 29 ± 3 | 37 ± 2 | 1.36 |
| 9A* | glass | MY-720/TE-pAB | 154 | — | 10.6 ± .1 | 0.33 ± .00 | 7 ± 1 | 6 ± 1 | 4.05 |

*not according to this invention
$^a$7 Days in deionized H$_2$O at 82° C.
$^b$13 Days in deionized H$_2$O at 71° C.

| Sample | | | % Cured | Tg (°C.) |
|---|---|---|---|---|
| 1 | | Graphite MY-720 FD-1 | 88 | 197 |
| 2* | | Graphite MY-720 DDS | 82 | 197 |
| 3* | | Graphite MY-720 DP-mAB | 87 | 182 |
| 4* | | Graphite MY-720 TE-pAB | 93 | 127 |
| 5* | | Graphite MY-720 pDMP-mAB | 95 | 184 |

*not according to this invention

The results of Test (I) show that all the compositions were cured to similar extents (except for DDS which was somewhat undercured). The glass transition temperatures of resin composites containing DP-mAB, TE-pAB and pDMP-mAB are lower than those containing DDS and FD-1. This means that the DP-mAB, TE-pAB and pDMP-mAB examples will not have the high temperature capability of the composite cured with FD-1.

The following additional tests were carried out, with the results seen on Table 1 (infra.):

(II) Dynamic Mechanical Analysis

Using a DuPont Dynamic Mechanical Analyzer 982, a characteristic temperature was measured on the laminates. The temperature at which the loss properties (tan δ) are a maximum is designated Tg. This method is

EXAMPLES 11–13

Three fiber resin matrix formulations were prepared from the following materials:

| component (a) | CELION ® 6K high strain graphite fiber |
|---|---|
| component (b)(i) | ARALDITE ® MY720 |
| | EPON ® 1031 (see formulae, supra.) |
| curing agent (ii) | trimethylene bis-(p-aminobenzoate) |
| curing co-agent | diamino diphenyl sulfone (DDS) |
| polymer modifier | acrylonitrile-butadiene-styrene core-shell polymer |
| catalyst | reaction product of toluene-2,4-diisocyanate with dimethyl amine |
| filler | fumed colloidal silica (Cab-O-Sil ® M-5, Cabot Corp.). |

Figure 2:
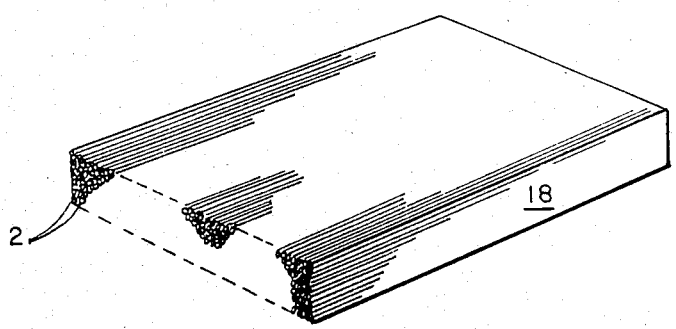
FIG. 2 is an enlarged cross-sectional view of a strip of the fiber resin matrix prepreg tape of the invention.

Using an apparatus shown generally in FIG. 1, prepreg tapes of the structure shown generally in FIG. 2 were prepared:

|  | EXAMPLES | | |
|---|---|---|---|
| (28%) Resin mixture (parts by weight) | 11 | 12 | 13 |
| N,N,N',N'—tetra(glycidyl-4,4'-diaminodiphenyl)methane | 80 | 80 | 80 |
| Tetraglycidoxy tetraphenylethane | 20 | 20 | 20 |
| Trimethylene bis-(para-aminobenzoate) | 44 | 44 | 65 |
| Diamino diphenyl sulfone | — | — | 20 |
| Polymer modifier* | — | 5 | — |
| Catalyst | 1 | 1 | 1 |
| Fumed silica | 6 | 6 | 6 |
| (72%) Filament (parts by weight) | | | |
| 6K graphite fibers having a strain to failure of about 1.5%. | | | |

*BLENDEX 311, Borg-Warner Co.

These samples were cured and compared against commercial fiber resin matrixes. Laminates were prepared and tested as follows:

| Test | Laminate Composition |
|---|---|
| Uni-Comp | 8 sheets [0] |
| Quasi-Comp | 16 sheets [(±45/0/9)$_2$]$_s$ |
| Comp/Impact | 36 sheets [(±45/0/90/0/90$_2$−/+45/0/−90/+45]$_s$ |

The compression strength was measured on a modified ASTM D695 specimen described in D. H. Woolsencraft, et al., Composites, October 1981, pages 275–280. Both unidirectional and quasi-isotropic laminates were tested by this method. Compressive strength after impact was measured as described in B. A. Byers, NASA Report No. CR 159293, August, 1980. This property is tested by subjecting a cured laminate specimen to 1500 in.-lb. per inch of nominal thickness impact with a 0.62 in. diameter spherical tip impacter while supported by a rigid base (with a 3"×5" cutout). The panel is then tested in compression. Conditioning before testing is described by the phrases "wet" and "dry". "Wet" refers to conditioning for two weeks at 71° C., immersing in distilled water, prior to testing at 93° C. "Dry" means testing a sample, as prepared, at 23° C. The laminates tested and the results obtained are set forth in Table 2:

EXAMPLES 14–15

Following the general procedure of Examples 11–13, two prepregs were prepared using CELION ® high strain graphite fiber and the following epoxy resin composition:

|  | EXAMPLE | |
|---|---|---|
| COMPOSITION (parts by weight) | 14 | 15 |
| N,N,N',N'—tetraglycidyl-4,4'-diamino diphenyl methane | 100 | 100 |
| Trimethylene bis(p-aminobenzyoate) | 48.4 | 48.4 |
| Resin modifier (Union Carbide PKHH)* | 10 | 10 |
| Reaction product of toluene-2,4-diisocyanate with dimethyl amine (catalyst) | 1 | — |
| Boron trifluoride complex with ethyl amine (catalyst) | — | 0.5. |

*PKHH:

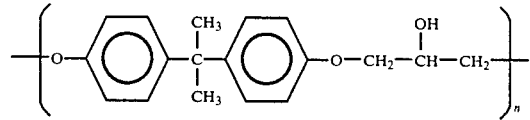

The prepregs had a resin content of 28% and a graphite fiber content of 72%, by weight. Thirty-six plies were consolidated under heat and pressure into a unidirectional laminate at 150° F. for 1 hour and 350° F. for 2 hours. Compression strength after impact was measured, using an impact of 1500 in.-lb. per inch of thickness, with the following results: Example 14, 34 ksi, and Example 15, 33 ksi, demonstrating excellent properties in this respect.

EXAMPLE 16

Bisphenol A diglycidyl ether plus oligomers (EPON ® 828, Shell Chemical Co.) was mixed with trimethylene bis(p-aminobenzoate) at a ratio of 1.0 epoxy equivalents to 0.75 amine equivalents (wt. ratio: 94.9 g. to 30.1 g.). The resin was coated onto graphite fiber (CELION ® 6K high strain graphite fiber) and cured into unidirectional 8-ply laminates by heating at

TABLE 2

| EXAMPLE | CONDITION | UNI-COMP | | QUASI-COMP | | COMPRESSIVE STRENGTH AFTER IMPACT (KSI) |
|---|---|---|---|---|---|---|
|  |  | 23° C. | 93° C. | 23° C. | 93° C. | 1500 in.-lb./in. |
| 11 | dry* | 189 | 205 | 84 | 93 | 31.5 |
|  | wet* | — | 126 | — | 71 |  |
| 12 | dry | 206 | 178 | 87 | 82 | 32.0 |
|  | wet | — | 130 | — | 61 |  |
| 13 | dry | 205 | 171 | 92 | 74 | 36.0 |
|  | wet | — | 12 to 140** | — | 45 |  |
| Commercial No. 1 | dry | — | — | — | — | 41 |
| Commercial No. 2 | dry | 180 | 175 | 83 | 78 | 28.5 |
|  | wet | — | 145 | — | 69 |  |
| Commercial No. 3 | dry | — | — | — | — | 20.6 |

*"dry" = as - prepared sample tested at RT and 93° C. ("hot") "wet" = sample immersed two weeks in water at 71° C.
**mean = 34. For best hot/wet compression strength it would appear that small to moderate excesses of amine are preferred.

Figure 3:
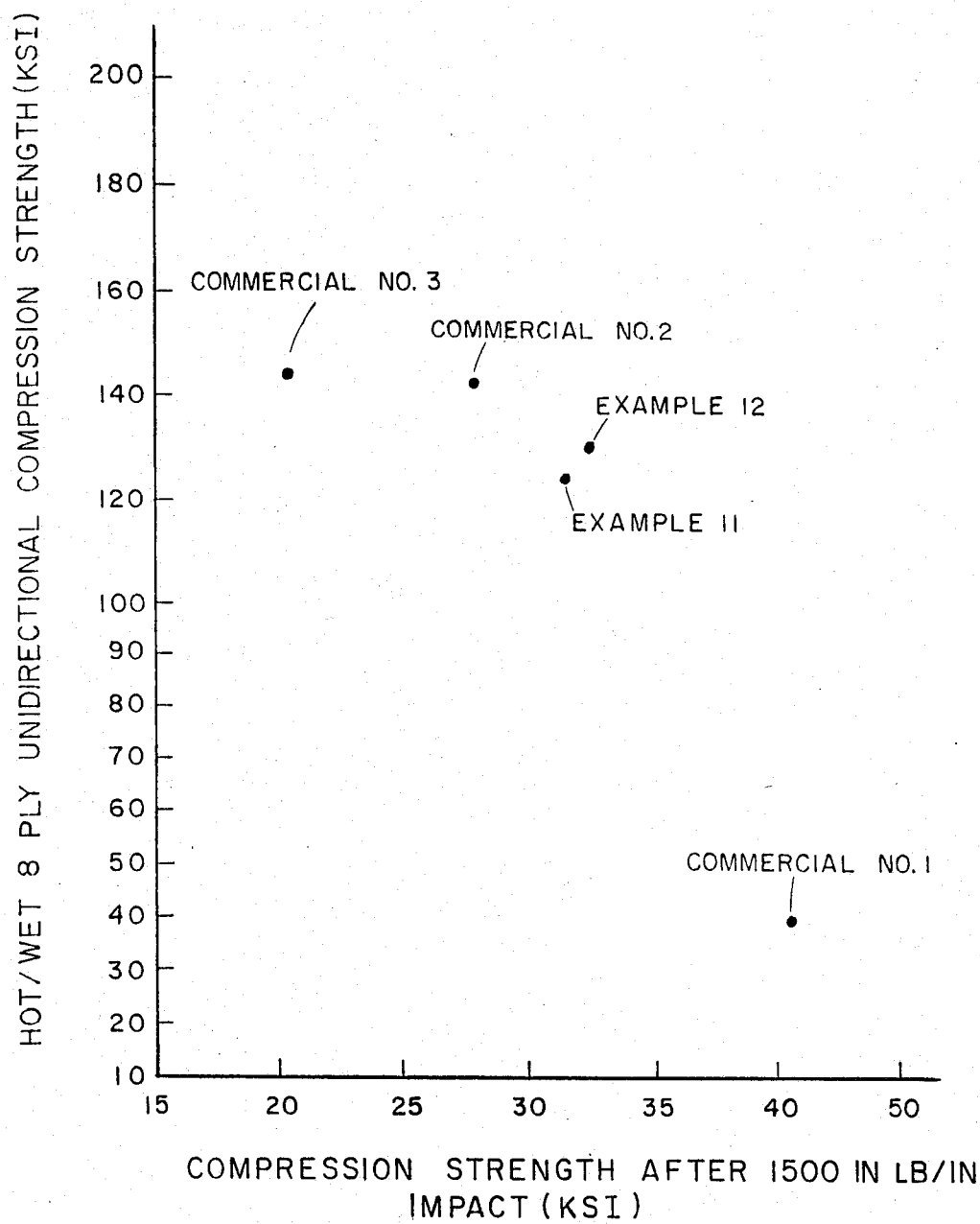
FIG. 3 is a graphical representation comparing hot/wet compression strength versus dry impact strength for composites according to this invention with state-of-the-art composites.

Some of the foregoing data are represented graphically also in FIG. 3. The data demonstrate that reinforced composites according to this invention compare favorably with commercially available fiber resin matrices, e.g., Examples 11 and 12 show higher compression strength after impact than two of the three commercial compositions tested, and better hot/wet compression strength than one of them.

350° F. for 2 hours. The interlaminar strain energy release rate was 5.0 in.-lb./sq. in.

EXAMPLE 17

Bisphenol A diglycidyl ether and oligomers (DER ® 331, Dow Chemical Co.) was mixed with N,N-dimethyl trimethylene-bis(p-aminobenzoate) at a ratio of 1.0 epoxy equivalents to 0.75 NH—amine equivalents (weight ratio: 75.9 g. to 52.3 g.). The resin was coated onto graphite fabric (CELION® 3K70, plain weave) and cured to a 10-ply laminate by heating at 350° F. for 2 hours. Good quality laminates according to this invention were produced.

EXAMPLE 18

A mixture comprising tris(4-glycidoxyphenyl) diglycidyl methane (80 parts, Dow Chemical XD-7342), bisphenol A diglycidylether (20 parts, Dow Chemical DER® 331), trimethylene bis(p-aminobenzoate), 28 parts, dicyandiamide, 2 parts, and the reaction product of 2,4-toluene diisocyanate and dimethylamine, 2 parts, all by weight, was prepared and applied to CELION® high strain graphite fibers and made into an 8-ply unidirectional laminate.

EXAMPLE 19

Tris-(4-glycidoxyphenyl) methane (Dow Chemical, XD-7342) was mixed with N,N'-dimethyltrimethylene bis(p-aminobenzoate) at a ratio of 1.0 epoxy equivalents to 0.75 amine equivalents (weight ratio: 69.8 g. to 55.2 g.). The resin was coated onto graphite fabric (CELION® 3K70, plain weave) and cured into a 10-ply laminate by heating at 350° F. for 2 hours. Good quality laminates according to this invention were produced.

EXAMPLE 20

An epoxylated novolac (Dow Chemical DEN® 438) was mixed with trimethylene bis-(p-aminobenzoate) at a ratio of 1.0 epoxy equivalent to 0.75 amine equivalents (weight ratio: 78.9 g: 26.1 g). The resin was coated onto graphite fabric (CELION® 3K70, plain weave) and cured into a 10 ply laminate by heating at 350° F. for 2 hours. Good quality laminates according to this invention were produced.

EXAMPLE 21

The procedure of Example 20 was repeated, substituting for the diamine, N,N'-dimethyl trimethylene bis(p-aminobenzoate) (weight ratio: 72.7 g. epoxy to 52.3 g. diamine). Good quality laminates according to this invention were produced.

EXAMPLE 22

Bisphenol A diglycidyl ether (DER® 331, Dow Chemical Co.) was mixed with 1,3-trimethylene (p-aminobenzoate) at a weight ratio of 94.9 g. epoxide to 30.1 g. diamine. The resin was coated onto polyaramid satin weave fabric (DuPont KEVLAR® 285K) and cured into a 6-ply laminate by heating at 350° F. for 2 hours. Good quality composites according to this invention were obtained.

EXAMPLE 23

The procedure of Example 22 was repeated, substituting for the diamine, N,N'-dimethyl trimethylene bis(p-aminobenzoate) (weight ratio 75.9 g. epoxy to 52.3 g.). Good quality composites were obtained.

EXAMPLE 24

The procedure of Example 22 was repeated, except that the resin mixture was coated onto nickel-plated graphite fibers instead of polyaramid cloth. The matrix composition was cured into ¼"×10"×⅛" composite rods by heating at 350° F. for two hours. Good quality composites were obtained.

EXAMPLE 25

The procedure of Example 23 was repeated, except that the resin mixture was coated onto nickel-plated graphite fibers instead of polyaramid cloth. The matrix composition as cured into ¼"×10"×⅛" composite rods by heating at 350° F. for two hours. Good quality composites were obtained.

EXAMPLE 26

A resin composition is prepared by mixing the following:

| | Amount (parts by wt.) |
| --- | --- |
| N,N,N',N'—tetraglycidyl-4,4'-diamino diphenyl methane | 120 |
| Polyether polyimide resin (General Electric ULTEM)* | 15 |
| Trimethylene bis(p-aminobenzoate) | 48 |
| Boron trifluoride - ethylamine complex | 0.5 |

*ULTEM:

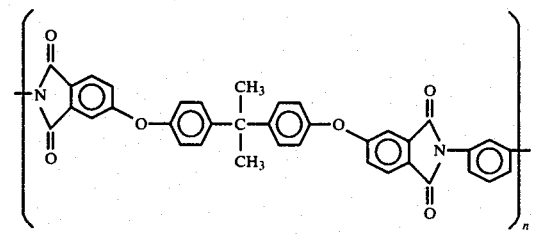

A prepreg tape is prepared following the general procedure of Examples 11-13, with a 35% to 45%, preferably 40%, resin-55% to 65%, preferably 60%, graphite loading. When this is formed into laminates by the procedure of Examples 11-13, excellent quality composites are produced. Preferred ranges for the components of the compositions are, (a), 114–126 parts; (b), 14.25–15.75 parts; (c) 45.6–50.4 parts; and (d), 0.475–0.525 parts (by weight).

The above-mentioned patents, applications and publications are incorporated herein by reference. It is seen that the present invention produces articles of manufacture with beneficial properties, making them useful in a variety of applications. Many variations will suggest themselves to those skilled in this art in light of the foregoing detailed description. All such obvious variations are within the full intended scope of the appended claims.

What is claimed is:

1. A fiber resin matrix composition comprising:
   (a) non-siliceous reinforcing filaments, and
   (b) a heat-curable epoxy resin composition comprising:
      (i) an epoxy prepolymer or combination of prepolymers having more than one epoxide group per molecule, and
      (ii) an amount effective to promote cure of an amine-functional curing agent or combination of curing agents selected from those of the formula:

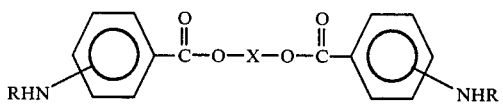

wherein R is hydrogen or methyl and X is a divalent non-aromatic organic hydrocarbon, non-aromatic hetero-interrupted hydrocarbon, or non-aromatic halo- or alkyl-substituted hydrocarbon radical, wherein the structure of X is characterized by conferring on composites comprised of said fiber resin matrix composition improved interlaminar toughness and residual compression strength after impact, while maintaining compression strength under hot/wet conditions.

2. A composition as in claim 1, wherein X is a divalent radical selected from the group consisting of polymethylene of from 2 to 10 carbon atoms; —(CH$_2$CH$_2$OCH$_2$CH$_2$OCH$_2$CH$_2$)—; —CH$_2$CH$_2$OCH$_2$CH$_2$—;

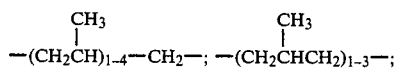

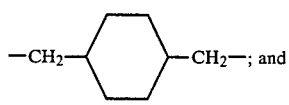

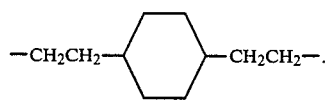

3. A composition as in claim 2, wherein said curing agent (b)(ii) is selected from compounds of the formula:

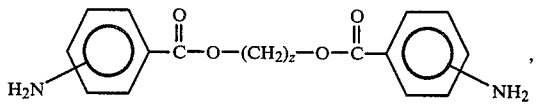

wherein z is an integer of from 2 to 6.

4. A composition as in claim 3, wherein said curing agent (b)(ii) comprises a compound of the formula:

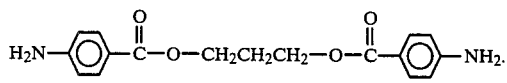

5. A composition as in claim 2, wherein said curing agent (b)(ii) is selected from compounds of the formula:

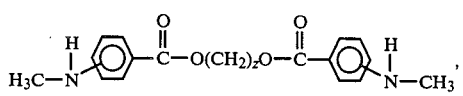

wherein z is an integer of from 2 to 6.

6. A composition as in claim 5, wherein said curing agent (b)(ii) comprises a compound of the formula:

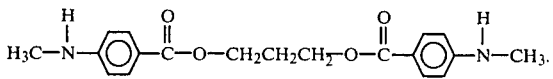

7. A composition as defined in claim 2 wherein curing agent (b)(ii) comprises a mixture of a compound of the formula:

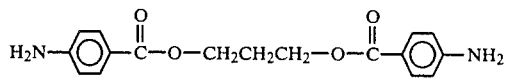

and a compound of the formula:

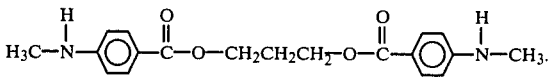

8. A composition as in claim 1, wherein said curing agent (b)(ii) is used in combination with a second aromatic polyamine curing agent.

9. A composition as in claim 8, wherein said second aromatic polyamine is selected from diamino diphenyl sulfone, bis-3-aminophenoxy diphenyl sulfone, bis-4-aminophenoxy diphenyl sulfone, diaminobenzoate methylene dianiline or phenylene diamine.

10. A composition as in claim 1, wherein said non-siliceous filaments (a) comprise carbon, silicon carbide, boron, rayon, polybenzimidazole, polybenzothiazole, polyester, polyamide, metal coated such filaments or a combination of any of the foregoing.

11. A composition as in claim 10, wherein said filaments comprise graphite filaments, polyaramid filaments or nickel-plated graphite filaments.

12. A composition as in claim 1, wherein the epoxy prepolymer (b)(i) is a cycloaliphatic polyepoxide.

13. A composition as in claim 1, wherein the epoxy prepolymer (b)(i) is selected from aromatic compounds of the formula:

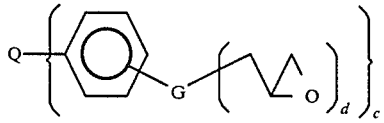

and halogen and alkyl substituted derivatives of such compounds, wherein c is 2, 3 or 4 and equal to the valence of Q, Q is a divalent, trivalent or tetravalent radical; G is —O—, —NR'—or

R' is hydrogen or alkyl; and d is 1 or 2 and equal to 1 less than the valence of G.

14. A composition as in claim 13, wherein the epoxy prepolymer (b)(i) comprises a compound of the formula:

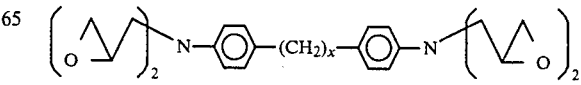

wherein x is an integer of from 1 to 4.

15. A composition as in claim 14, wherein x is 1.

16. A composition as in claim 13, wherein the epoxy prepolymer (b)(i) comprises a compound of the formula:

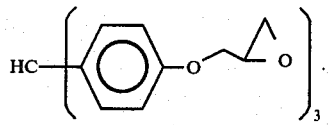

17. A composition as in claim 13, wherein the epoxy prepolymer (b)(i) comprises a compound of the formula:

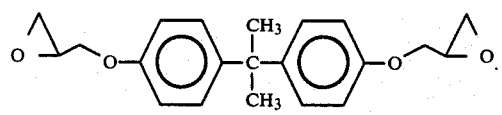

18. A composition as in claim 13, wherein the epoxy prepolymer (b)(i) comprises a compound of the formula:

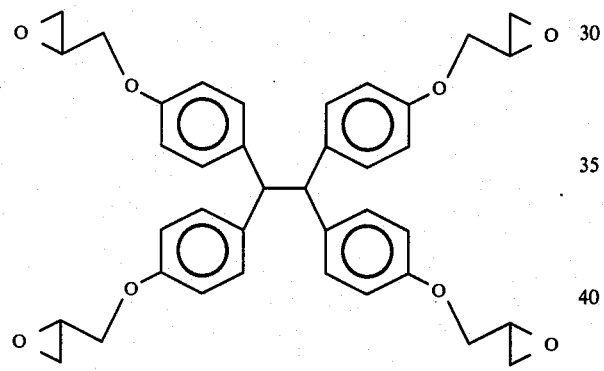

19. A composition as in claim 13, wherein the epoxy prepolymer (b)(i) comprises a compound of the formula:

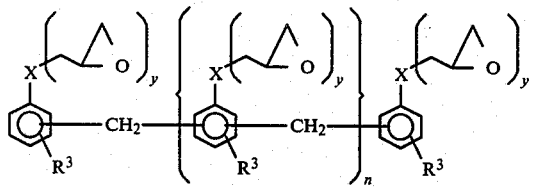

wherein y is 1 or 2, X is —O— or

$R^3$ is H or $CH_3$ and n is 2 to 8, or a mixture of the foregoing.

20. A composition as in claim 13, wherein the epoxy prepolymer (b)(i) comprises a compound of the formula:

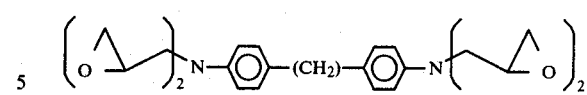

in combination with a compound of the formula:

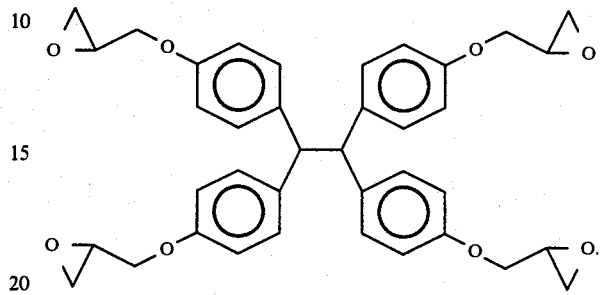

21. A composition as in claim 13, wherein the epoxy prepolymer (b)(i) comprises a compound of the formula:

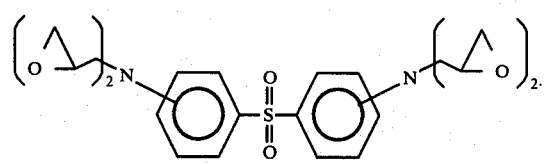

22. A composition as in claim 13, wherein component (b) comprises materials with the following parts by weight allocation:
from about 75 to 125 parts (b)(i), and
from about 30 to 50 parts (b)(ii).

23. A composition as in claim 1, which additionally contains in (b) a filler.

24. A composition as in claim 23, wherein the filler is fumed silica.

25. A composition as in claim 1, which also includes in (b) a small effective amount of a curing catalyst.

26. A composition as in claim 25, wherein the catalyst comprises the reaction product of toluene diisocyanate and dimethyl amine or the reaction product of boron trifluoride and an amine.

27. A composition as in claim 1, which also includes a minor, effective, property-modifying amount of a bis-maleimide compound or a styrene-butadiene-acrylonitrile core-shell polymer.

28. A composition as in claim 27, wherein the bis-maleimide compound is of the formula:

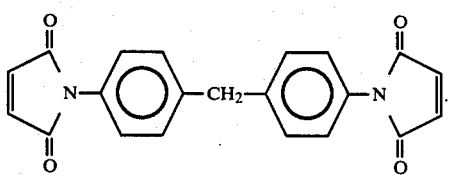

29. A heat-curable epoxy resin composition comprising a non-siliceous fiber reinforcement and
(i) an epoxy prepolymer or combination of prepolymers having more than one epoxide group per molecule, and (ii) an amount effective to promote cure of an amine-functional curing agent or combination of curing agents selected from compounds of the formula:

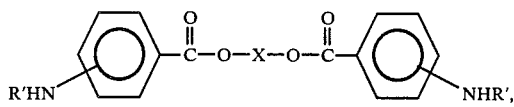

wherein R' is hydrogen or methyl, and X is a divalent non-aromatic organic hydrocarbon, non-aromatic hetero-interrupted hydrocarbon, or non-aromatic halo- or alkyl-substituted hydrocarbon radical, wherein the structure of X is characterized by conferring on composites comprised of said epoxy resin composition improved interlaminar toughness and residual compression strength after impact, while maintaining compression strength under hot/wet conditions.

30. A composition as in claim 29, wherein X is selected from the group consisting of polymethylene of from 2 to 10 carbon atoms, —CH$_2$CH$_2$OCH$_2$CH$_2$—, —CH$_2$CH$_2$CH(CH$_3$)CH$_2$CH$_2$—, —CH$_2$CH(CH$_3$)CH$_2$CH$_2$CH$_2$—, —CH$_2$CH$_2$OCH$_2$CH$_2$OCH$_2$CH$_2$—,

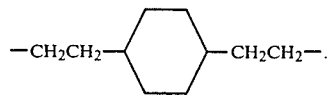

-continued

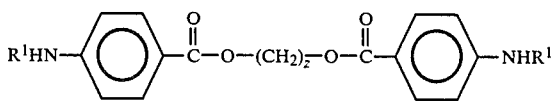

31. A composition as in claim 29, which additionally contains one or more components selected from the group consisting of aromatic amine curing co-agents, curing catalysts, fillers, thermoplastic modifiers, rubber modifiers, and bismaleimide modifiers.

32. A composition as in claim 29, wherein, in component (ii), X is —CH$_2$CH$_2$CH$_2$—.

33. A composition as in claim 32 wherein, in component (ii), R' is methyl.

34. A heat-curable epoxy resin composition comprising a non-siliceous reinforcement and
(i) an epoxy prepolymer or combination of prepolymers having more than one epoxide per molecule, and
(ii) an amount effective to promote cure of an amine-functional curing agent or combination of curing agents selected from those of the formula:

$$R^1HN-\bigcirc-\overset{O}{\underset{\|}{C}}-O-(CH_2)_z-O-\overset{O}{\underset{\|}{C}}-\bigcirc-NHR^1$$

wherein R$^1$ is hydrogen or methyl, and z is an integer of from 2 to 12.

35. A composition as in claim 29, wherein said reinforcement comprises carbon filaments.

36. A composition as in claim 29, wherein said reinforcement comprises graphite filaments.

* * * * *